(12) United States Patent
Stonefield et al.

(10) Patent No.: US 9,414,804 B2
(45) Date of Patent: Aug. 16, 2016

(54) DIAGNOSTIC IMAGING DEVICE HAVING PROTECTIVE FACADE AND METHOD OF CLEANING AND DISINFECTING SAME

(75) Inventors: Andrew David Stonefield, Whitefish Bay, WI (US); Liu Lanping, Jiangsu (CN); Aurelie Roncaglioni, Buc (FR)

(73) Assignee: General Electric Company, Schenectady, NY (US)

( * ) Notice: Subject to any disclaimer, the term of this patent is extended or adjusted under 35 U.S.C. 154(b) by 2169 days.

(21) Appl. No.: 11/895,346

(22) Filed: Aug. 24, 2007

(65) Prior Publication Data

US 2009/0054781 A1  Feb. 26, 2009

(51) Int. Cl.
*A61B 8/00* (2006.01)
*A61B 8/08* (2006.01)
*A61B 5/055* (2006.01)
*A61B 6/00* (2006.01)

(52) U.S. Cl.
CPC . *A61B 8/00* (2013.01); *A61B 8/461* (2013.01); *A61B 8/467* (2013.01); *A61B 8/483* (2013.01); *A61B 5/055* (2013.01); *A61B 6/00* (2013.01); *A61B 6/4423* (2013.01); *A61B 2562/247* (2013.01)

(58) Field of Classification Search
USPC ........... 600/459; 128/846; 134/3, 6, 7, 26, 42; 345/175
See application file for complete search history.

(56) References Cited

U.S. PATENT DOCUMENTS

| | | | |
|---|---|---|---|
| 4,937,499 A * | 6/1990 | Hunte | 315/149 |
| 5,145,523 A * | 9/1992 | Halpin et al. | 510/407 |
| 5,295,485 A * | 3/1994 | Shinomura et al. | 600/443 |
| 5,640,609 A * | 6/1997 | Reibl et al. | 396/25 |
| 5,657,210 A * | 8/1997 | Yamanaka | 361/814 |
| 5,865,650 A * | 2/1999 | Marian et al. | 439/638 |
| 6,991,490 B1 * | 1/2006 | Su | 439/521 |
| 7,907,394 B2 * | 3/2011 | Richardson et al. | 361/679.3 |
| 2003/0151809 A1 | 8/2003 | Takahashi et al. | |
| 2003/0195644 A1 | 10/2003 | Borders et al. | |
| 2006/0114245 A1 * | 6/2006 | Masters et al. | 345/175 |
| 2007/0085157 A1 | 4/2007 | Fadell et al. | |
| 2009/0043195 A1 * | 2/2009 | Poland | 600/437 |

FOREIGN PATENT DOCUMENTS

WO   WO 2006/060455 A1   6/2006

OTHER PUBLICATIONS

PCT International Search Report, International Application No. PCT/US2006/067314, International Filing Date: Jun. 18, 2008, Applicant: General Electric Company, (3) pgs.

* cited by examiner

*Primary Examiner* — Jonathan Cwern
(74) *Attorney, Agent, or Firm* — Dean D. Small; The Small Patent Law Group, LLC

(57) ABSTRACT

A diagnostic imaging device is provided that includes a display panel, a set of switches including at least one of a proximity switch and a capacitive switch, and a one-piece non-flexible facade covering the display panel and the set of switches. The facade is transparent over at least a portion of the display panel and configured such that the set of switches are operable by a user. A method for cleaning the imaging system includes operating the diagnostic imaging device, including the set of switches, by touching the one-piece non-flexible facade with human fingers or a stylus over selected switches, and, after said operating the diagnostic imaging device, disinfecting the diagnostic imaging device by cleaning the one-piece non-flexible facade with quaternary ammonium or isopropyl alcohol, or both.

33 Claims, 6 Drawing Sheets

DIAGNOSTIC IMAGING DEVICE HAVING PROTECTIVE FACADE AND METHOD OF CLEANING AND DISINFECTING SAME

BACKGROUND OF THE INVENTION

This invention relates generally to diagnostic imaging devices, and more particularly, to devices and apparatus that facilitate the cleaning and disinfecting of diagnostic imaging devices.

Diagnostic imaging devices such as ultrasound imaging devices require a user interface to control scanning operation and a display screen to view images being scanned. Usually, these devices have a separate console and display screen, but some devices include a box or tablet shaped scanner, with buttons adjacent the display screen. In either embodiment, there are physically separate components joined together to form the device.

In the case of an ultrasound imaging device, a display screen is used to view images produced by a probe and processed on electronic circuit boards of the device. In newer systems, the screen is often a flat panel framed in plastic without any other protection against chemicals or fluid splatter. The display screen surface itself may be damaged by repeated application of harsh chemicals and any fluid material that comes in contact with the display screen may seep into corners and edges of the frame, thereby potentially damaging the display screen or circuitry inside the device.

With known imaging devices using multiple components, there are part lines or seams where components join together, further increasing the risk of contamination by infectious diseases and/or bacteria in a medical environment in which a diagnostic imaging device may be employed. A similar risk of contamination is posed around key pads, mechanical buttons, trackballs, touch pads, etc., that are part of the diagnostic imaging device.

Cleaning the seams between all the components is a dirty task that may have to be performed daily by a biomedical engineer or other employee of a health facility in meticulous detail. However, there is a risk that the equipment may not be totally cleaned because small splatters of blood and other bodily fluids go unseen. To ameliorate this problem, flexible plastic films or sheets that that can be layered onto consoles and keyboards have been used.

Health facilities are now starting to report incidents of infection that occur during a patient's hospital stay and ultrasound usage in intensive care unit operating rooms for anesthesia, vascular line placement and other surgical procedures is increasing. In some cases, ultrasound scanners are considered too contaminated to place close to a patient during an operating room procedure. In other cases, to avoid infection and make cleaning simpler, the diagnostic imaging device is covered with plastic drapes or keyboard covers. However, these drapes or covers tend to interfere with the visibility of images and the operation of the imaging devices and may not always be completely effective in eliminating contamination. In still other cases, imaging devices are placed outside of the sterile field. However, the user then may have to twist and strain just to see an image and an additional person may be required to operate the imaging device.

BRIEF DESCRIPTION OF THE INVENTION

In accordance with an embodiment of the present invention, a diagnostic imaging device is provided that includes a display panel, a set of switches including at least one of a proximity switch and a capacitive switch, and a one-piece non-flexible facade covering the display panel and the set of switches. The facade is transparent over at least a portion of the display panel and configured such that the set of switches are operable by a user.

In accordance with another embodiment, a display unit for an imaging apparatus is provided. The display unit includes a display panel configured to display an image at the front of the imaging apparatus, a one-piece non-flexible facade covering the front of the apparatus and one of transparent and at least translucent over at least a portion of the display panel, and a set of switches operable without moving parts through the one-piece non-flexible facade using one of a human finger and a stylus.

In accordance with yet another embodiment, a method for operating and cleaning a diagnostic imaging device is provided. The diagnostic imaging device includes a display panel, a set of switches including at least one of a proximity switch and a capacitive switch, and a one-piece non-flexible facade covering the display panel and the set of switches. The facade is transparent over at least a portion of the display panel and allowing operation of the set of switches through the one-piece non-flexible facade using one of a human finger and a stylus. The method includes operating the diagnostic imaging device, including the set of switches, by touching the one-piece non-flexible facade with human fingers or a stylus over selected switches, and, after said operating the diagnostic imaging device, disinfecting the diagnostic imaging device by cleaning the one-piece non-flexible facade with quaternary ammonium or isopropyl alcohol, or both.

DETAILED DESCRIPTION OF THE INVENTION

Figure 1:
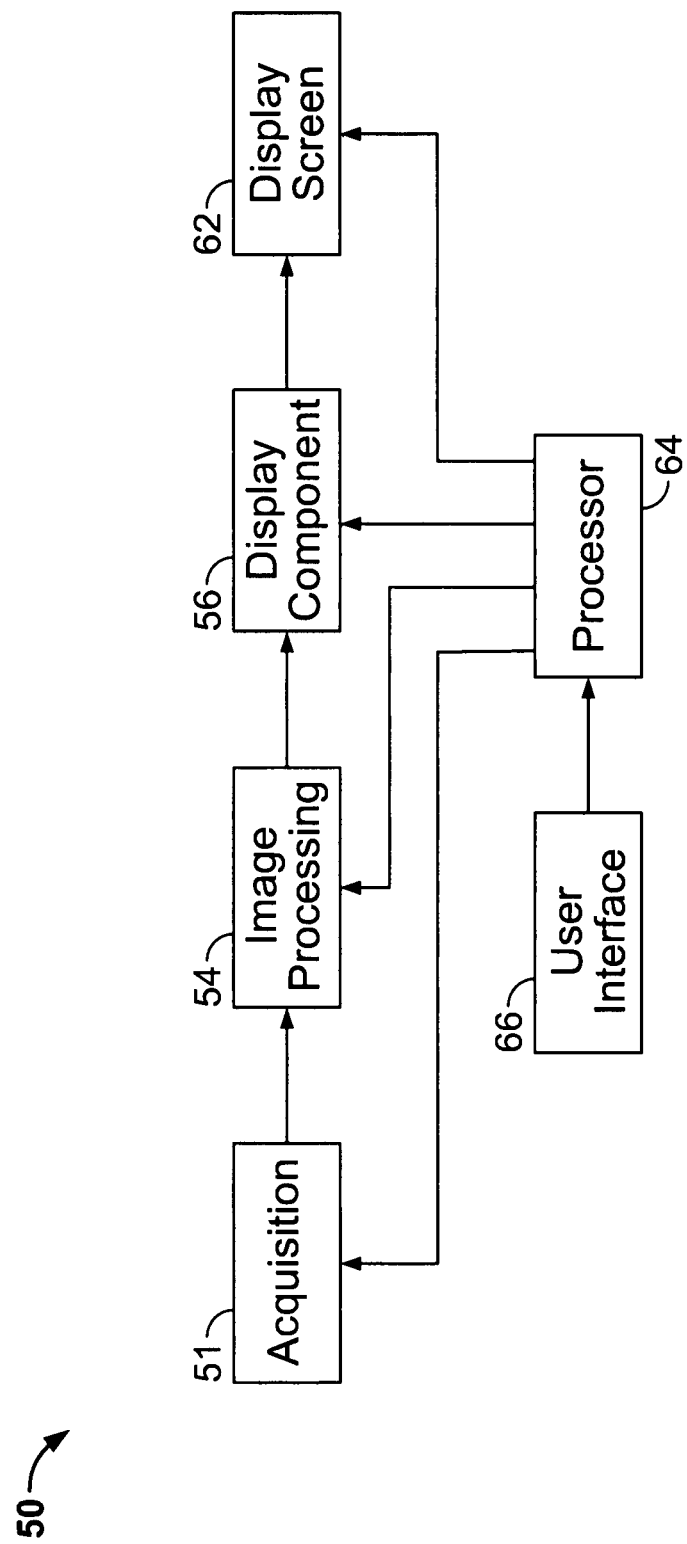
FIG. 1 is a block diagram of a diagnostic imaging device constructed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments of the invention provide a diagnostic imaging device 50 as shown in FIG. 1. The diagnostic imaging device 50 may be any type of system, for example, different types of medical imaging systems, such as an ultrasound imaging system, an x-ray imaging system, a computed-tomography (CT) imaging system, a single photon emission computed tomography (SPECT) system, a positron emission tomography (PET) imaging system, a nuclear medicine imaging system, a magnetic resonance imaging (MRI) system, and combinations thereof (e.g., a multi-modality imaging system), among others. However, the various embodiment are not limited to medical imaging systems or imaging systems for imaging human subjects, but may include non-medical systems for imaging non-human objects and for performing non-destructive imaging or testing, security imaging (e.g., airport security screening), etc.

The diagnostic imaging device 50 includes an acquisition component 51 configured to acquire image data (e.g., ultrasound image data). The acquisition component 51 in embodiments of the present invention can comprise a probe 52 (shown in FIG. 2) configured to scan or otherwise image an object or volume of interest. Acquisition component 51 is operatively connected to an image processing component 54. The image processing component 54 is any type of image processor capable of processing image data acquired from acquisition component 51, and may comprise software running on processor 64. Image processing component 54 is also operatively coupled to a display component 56. The display component 56, which may be a controller, configures or formats the processed image data for display on a display screen 62. The display screen 62 may be any type of screen capable of displaying images, graphics, text, etc. In various embodiments of the present invention, for example, display screen 62 may be a liquid crystal display (LCD) screen or a plasma screen, among others.

The processor 64 (e.g., computer) or other processing unit controls the various operations within the diagnostic imaging device 50. For example, the processor 64 may receive user inputs from a user interface 66 and display requested image data or adjust the settings for the displayed image data. For example, a user may provide manual brightness or contrast adjustment settings to change the display properties of the display screen 62 or other input to control the scanning operation of acquisition module 51.

Figure 2:
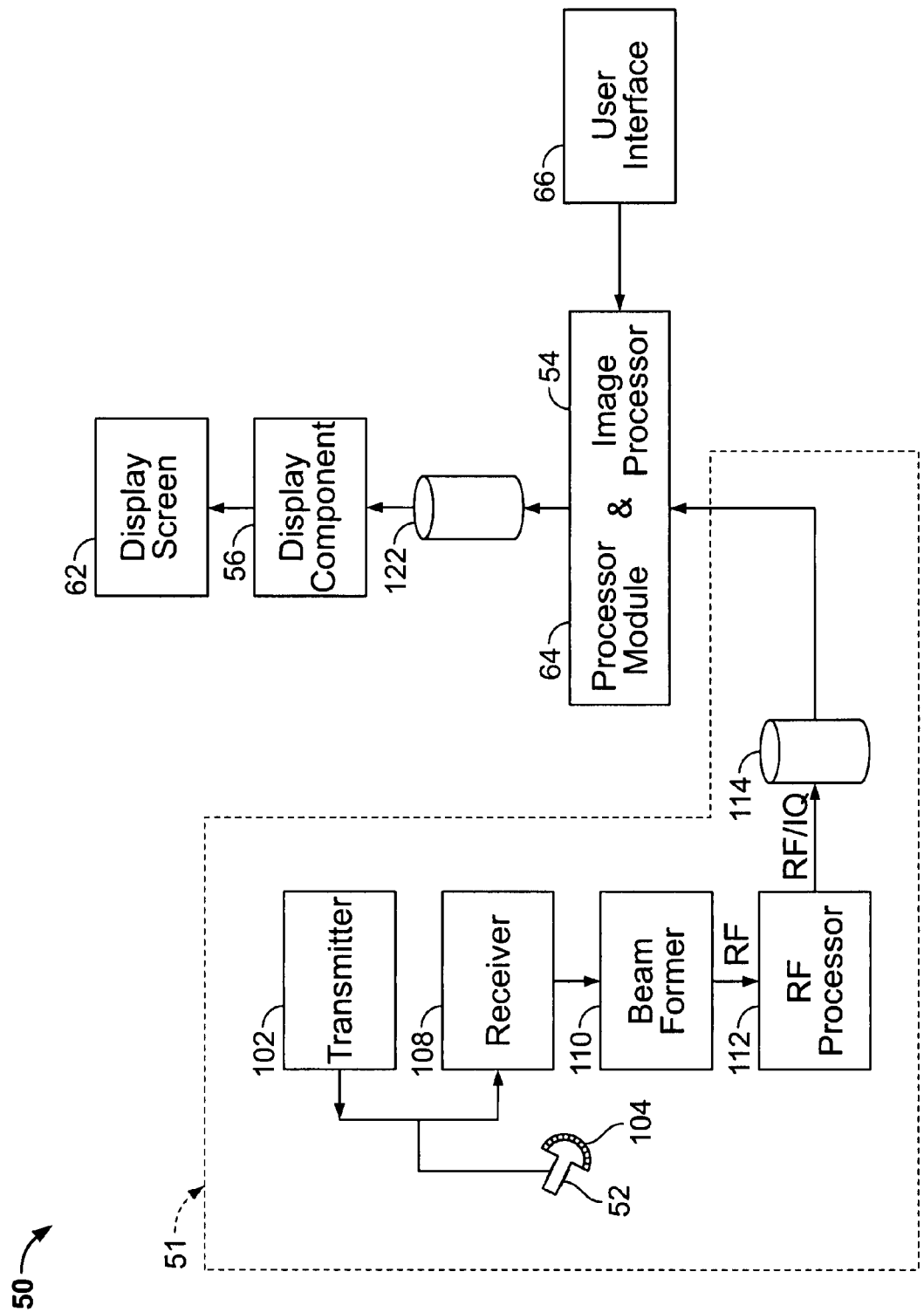
FIG. 2 is a block diagram of an ultrasound imaging system constructed in accordance with an embodiment of the invention.

In some embodiments, the diagnostic imaging device 50 is an diagnostic imaging device, such as shown in the schematic block diagram in FIG. 2. The acquisition module 51 includes one or more transmitters 102 that drive arrays of elements 104 (e.g., piezoelectric elements) within probe 52 to emit pulsed ultrasonic signals into a body. A variety of geometries may be used. The ultrasonic signals are back-scattered from structures in the body, like blood cells or muscular tissue, to produce echoes that return to the elements 104 of probe 52. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to a memory 114 for storage.

The diagnostic imaging device 50 also includes the processor 64 to process the acquired ultrasound information (e.g., RF signal data or IQ data pairs) and prepare frames of ultrasound information for display on display 62. The processor 64 is configured to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 during a scanning session and the processed and displayed in off-line operation. Image processing component 54 may comprise software that controls processor 64.

The processor 64 is connected to user interface 66 that may control operation of the processor 64. The display screen 62 includes one or more monitors that present patient information, including diagnostic ultrasound images to the user for diagnosis and analysis. One or both of memory 114 and memory 122 may store three-dimensional data sets of the ultrasound data, where such 3-D data sets are accessed to present 2-D and 3-D images. The images may be modified and the display settings of the display screen 62 may also be manually adjusted using the user interface 66 and display component 56 and/or processor 64 and/or image processing component 54.

The ultrasound system 50 may obtain volumetric data sets by various techniques (e.g., 3D scanning, real-time 3D imaging, volume scanning, 2D scanning with transducers having positioning sensors, freehand scanning using a voxel correlation technique, 2D or matrix array transducers and the like).

Figure 3:
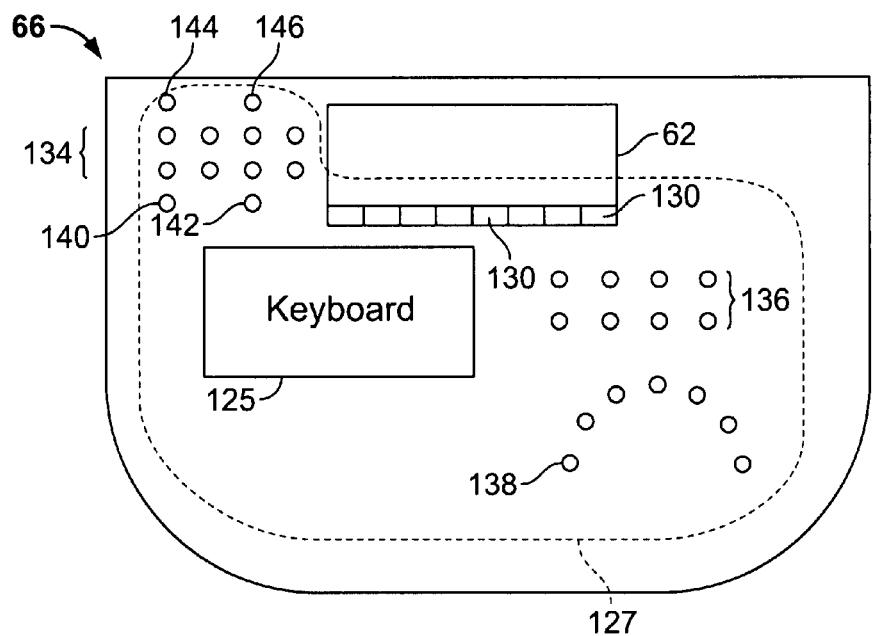
FIG. 3 is a top plan view of a user interface constructed in accordance with an embodiment of the present invention.

FIG. 3 illustrates the user interface 66 constructed in accordance with one embodiment of the invention. The user interface 66 includes a keyboard 126, a display screen 62, a series of soft keys 130 proximate the display screen 62, view position buttons 134, mode buttons 136 and control or operation keys 138. For purposes of the present invention, keyboard 125 soft keys 130, view position buttons 134, mode buttons 136, and control or operation keys 138 are all considered part of a plurality of user inputs referred to generically by the numeral 127. The soft keys 130 are assigned different functions on the screen 62 depending upon a selected examination mode, stage of examination and the like, and may include any or all of the following functions, and/or other functions: freeze, store, gain, depth, print, color, patient, measure, comment, Doppler, play, pause, archive, brightness, steer, and auto-optimize.

Mode buttons 136 are used to control the display of images on the display 62 and control various options, for example, zoom, rotate, viewing mode, examination mode, etc. For example, the view position buttons 134 may change different views of the displayed image. As a further option, the size, position and orientation of the displayed image may be controlled partially or entirely by the soft keys 130. User inputs 127 may comprise proximity switches, capacitive switches, or some combination thereof, or any other switches capable of operation with or without a stylus (not shown) or human figures through a plastic case without the buttons themselves having or needing moving parts. In some embodiments of the present invention, display 62 is made to simulate a touch screen by placing a matrix of such switches behind the display screen.

The user interface 66 also includes other controls as part of the plurality of user inputs 127, such as a save command/option button 140 and a restore command/option button 142 to save or restore certain image characteristics or changes to the displayed image. However, it should be noted that the various controls may be used to adjust or control different settings, display options, etc. For example, the user interface 66 may include a brightness control button 144 that allows a user to manually adjust screen brightness and a contrast control button 146 that allows a user to manually adjust screen contrast.

Some embodiments of the present invention provide a single piece construction of an impervious facade for the user interface 66 and display screen 62 of diagnostic imaging device 50, with no additional framing or peripheral buttons with moving parts for controlling device 50. The user interface 66 and display screen 62 are behind and protected by the facade to provide increased cleanability and durability. Some embodiments of the present invention utilize a clear polycarbonate plastic facade that is chemically resistant to common medical grade antibacterial and antiviral disinfecting agents and that does not degrade images displayed on the display screen. A chemically resistant facade is particularly useful in medical applications, in that it provides protection from fluid splatter and chemical cleaning agents and allows disinfection by quickly and easily wiping the facade clean after every use. The image quality of the display screen 62 is kept high and layered films and covers do not need to be installed. Furthermore, many embodiments of the present invention have no moving parts, no buttons to snap off, and no parts to loosen or come apart at the seams.

Active chemical cleaning and disinfectant ingredients used on probes and console materials and to which the chemically resistant facade is resistant include any or all of the following, and/or other ingredients, as well: glutaraldehyde, hydrogen peroxide, quaternary ammonia, peracetic acid, sodium dichloroisacyanurate, bleach (NaClO), ethanol, isopropanol, ortho-phthaldehyde (Cidex), ethylene glycol, bersteinsaure, O-phenylphenol, propylene glycol, ammonium chloride, and phenol.

Figure 4:
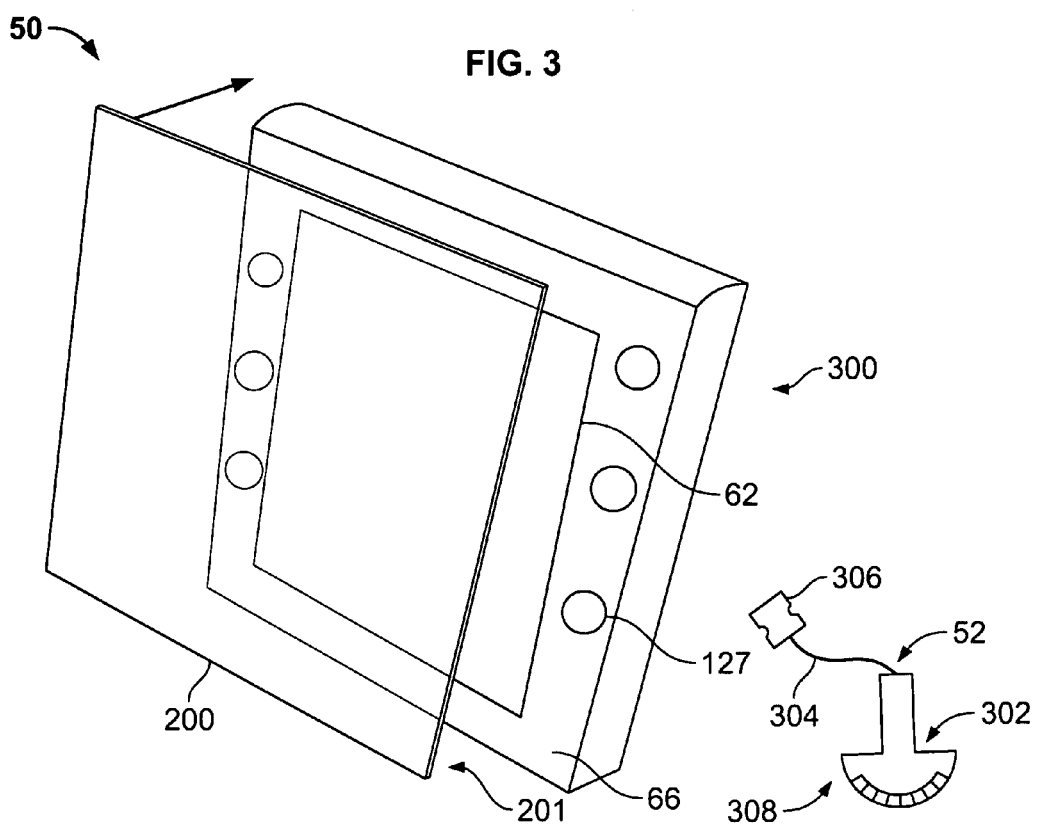
FIG. 4 is a pictorial drawing of a diagnostic imaging device embodiment of the present invention.

Thus, referring to FIG. 4, various embodiments of the present invention provide a diagnostic imaging device 50 (which may be a medical device such as an ultrasound imaging system) that includes a display panel 62, the plurality of user inputs 127 configured as one or more sets of proximity and capacitive switches (which may include alphabetic, numeric, symbolic, and/or special function keys) or any other switches without moving parts capable of operating from an internal side 201 of facade 200. A one-piece non-flexible facade 200 is also provided covering display panel 62 and user inputs 127, wherein facade 200 is transparent over at least a portion of display panel 62 and sufficiently thin such that covered proximity and/or capacitive switches in user interface 66 are operable by either human fingers (not shown) and/or a stylus (not shown).

For example, in one embodiment, hard keys and/or switches are capacitive buttons that react to the electrical touch of the finger through the plastic without the button having to respond to a moving element. A capacitive touch screen panel is coated with a material, typically indium tin oxide, that conducts a continuous electrical current across the sensor. The sensor therefore exhibits a precisely controlled field of stored electrons in both the horizontal and vertical axes—it achieves capacitance. The human body is also an electrical device which has stored electrons and therefore also exhibits capacitance. When the sensor's 'normal' capacitance field (its reference state) is altered by another capacitance field, e.g., someone's finger, electronic circuits located at each corner of the panel measure the resultant 'distortion' in the sine wave characteristics of the reference field and send the information about the event to the controller for mathematical processing. Capacitive sensors can either be touched with a bare finger or with a conductive device being held by a bare hand.

In one embodiment, scan operation of diagnostic imaging device 50 is performed by using a probe 52 in one hand and a control unit operated with the other (or by an assistant). A user can select, with his or her finger, a freeze, store, gain and/or depth capacitive keys during scanning to manipulate an image. Other capacitive hard keys that are available in some embodiments are used to change scan modes (from B-mode to Color), the steer a color box, auto-optimize image quality, and/or enter a patient screen or archive screen. A stylus is then used in some embodiments for mode precise inputs, like measuring, typing text on the onscreen graphic keyboard or editing stored files (archive).

For use in a medical environment, facade 200 in some embodiments is a transparent plastic that is a barrier to fluids, scratch resistant, and chemically resistant to repeated treatments of quaternary ammonium and isopropyl alcohol. A non-exhaustive list of such plastics include LEXAN® and CYCOLOY® plastics, both of which are available from General Electric Company, Schenectady, N.Y., but other clear polycarbonate plastics are also suitable. By being able to withstand repeated treatments of chemicals such as quaternary ammonium, isopropyl alcohol, and/or other chemicals, disinfection from at least the following infection vectors may be made possible: *micobacterium bovis* (tuberculosis), *staphylococcus aureus*, methicillin resistant *staphylococcus aureus* (MRSA), *salmonella choleraesuis, pseudomonas aeruginosa, escherichia coli* (*E. Coli*), influenza A2, herpes simplex virus type II, HIV-1, rhinovirus, *candida albicans, klebsiella pneumoniae*, methicillin, hepatitis B, vancomycin resistant enterococcus (VRE), vaccinia, and adenovirus.

Figure 5:
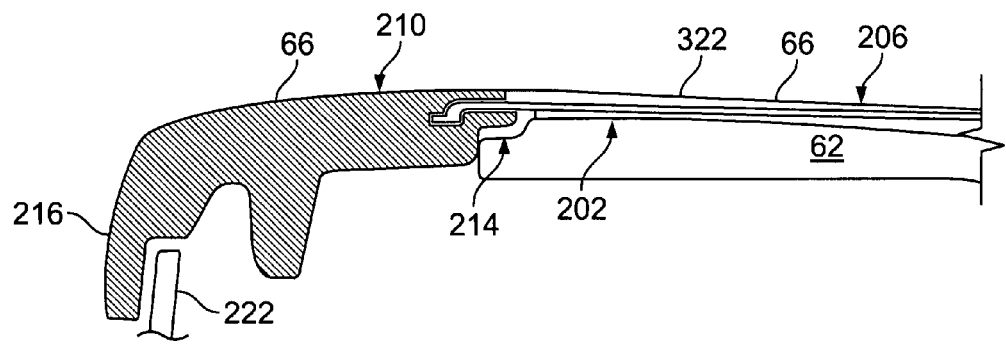
FIG. 5 is an enlarged sectional view of a portion of the diagnostic imaging device illustrated in FIG. 4, showing a rim and a painted area of the front facade in relation to the display screen of the imaging system.

Referring now to FIGS. 4 and 5, one-piece non-flexible facade 200 is thinner over display panel 62 and thicker over other covered areas in some embodiments to provide the clearest possible view of display panel 62. For example only and not by way of limitation, thicker areas may be 3 mm thick, while thinner areas may be 1.5 mm thick. Also, in some embodiments, one-piece non-flexible facade 200 has a fully transparent portion 206 over at least a portion 202 of display panel 62 and a painted or translucent (or both) portion 210 elsewhere. If painted, the painted portion 210 may have paint applied so that it is not exposed to the outside surface of facade 200. The painted or translucent portion 210 of facade 200 can, for example, have the aesthetic purpose of covering an edge 214 of display panel 62 and/or the application of labels to sensitive areas over individual user inputs 127, thereby showing where to press for keyboard lettering, scrolling, special functions, etc.

Figure 6:
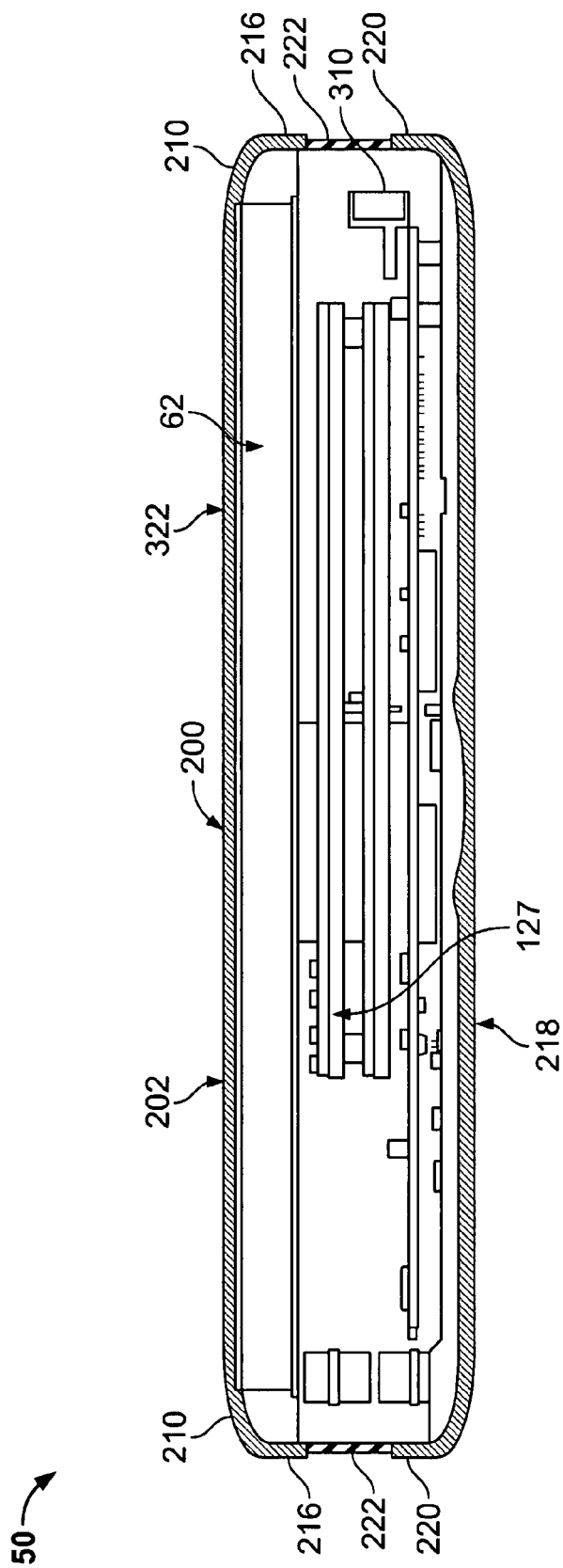
FIG. 6 is a cross-sectional view of an embodiment of a diagnostic imaging device of the present invention cut through the display screen.

FIG. 6 is a cross-sectional view of diagnostic imaging device 50 cut through display screen 62. Referring to FIGS. 4 through 6, some embodiments of diagnostic imaging device 50 include a one-piece non-flexible facade 200 with a rim 216, a one-piece rear facade 218 also having a rim 220, and a rubber belt 222 at least partially held in place under the rims 216 and 220 of facades 200 and 218. These embodiments effectively provide an impervious or nearly impervious enclosure for the other components of diagnostic imaging device 50 with a minimum of joints into which dirt, bacteria, viruses, liquids, etc. can be trapped, while allowing operation of and cleaning of diagnostic imaging device 50. One-piece rear facade 218 may be non-flexible and made of the same material as front facade 200, but need not be transparent. In some embodiments, capacitive hard keys are separate thin receptors laying between a clear single piece user interface cover and a hard internal frame/skeleton on the system. The hard keys can be LED backlit and wired to a circuit board or mother board in some embodiments.

Figure 7:
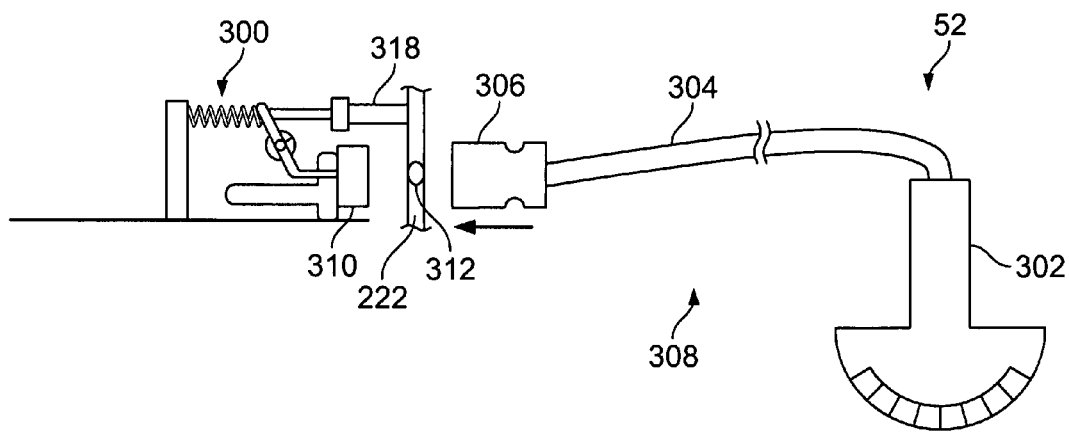
FIG. 7 is a close-up view of a portion of the diagnostic imaging device shown in FIG. 6 showing a connector and jack about to be sealingly connected.

In some embodiments of diagnostic imaging device 50 and referring to FIGS. 4, 6, and 7, diagnostic imaging device 50 is an ultrasound imaging apparatus that further includes a probe 52. The display panel 62, the user inputs 127, the one-piece non-flexible facade 200, the rubber belt 222, and the one-piece rear facade 218 comprise a first unit 300, and probe 52 further comprises a probe head 302, a probe cable 304, and a probe connector 306. Probe head 302, probe cable 304, and probe connector 306 together comprise a second unit 308 that is separable from the first unit 300. In addition, the first unit 300 further includes a sunken jack 310 and rubber seal 312 that are configured to sealingly receive the probe connector 306. For example, in one embodiment, probe connector 306 is received in a rubber seal 312 comprising a stretchable hole in rubber belt 222. This hole snaps back to form a gasket seal around probe connector 306 as connector 306 is pressed into jack 310. In some of these embodiments, sunken jack 310 further includes a mechanical push button 318 that is configured to eject probe connector 306. Push button 318 may itself be entirely covered by rubber belt 222 so as not to require any additional holes or seams.

In some embodiments of the present invention, unit 300 is a display unit for a diagnostic imaging device 50. Display unit 300 in some embodiments includes display 62 configured to display an image at a front surface 322 of diagnostic imaging device 50, a one-piece non-flexible facade 200 that is transparent or at least translucent over at least a portion 202 of display 62, and user inputs 126 operable without moving parts through the one-piece non-flexible facade 200 using human fingers and/or a stylus. In some embodiments, capacitive hard keys work as described above through the plastic facade. A supplied stylus uses an electromagnetic radio frequency signal between the chip in the stylus through to the touch panel attached to the LCD monitor beneath the plastic facade. These two methods allow the user to work controls through the plastic without moving parts in some embodiments.

It will be appreciated that embodiments of the present invention, with this single piece interface construction, can be quickly and easily wiped clean and disinfected. The industrial design of the surface segment in conjunction with the chemical resistant qualities of the material used provide effective protection against harsh medical grade antibacterial and antiviral disinfecting agents like quaternary ammonium and isopropyl alcohol. This allows a diagnostic device to be closer to both a patient, and to a user of the device, making the device easier to see and operate, even by a single user.

Also, the durability quality of the single piece construction reduces the chance of fluid splash entering the circuitry, possibly causing injury and damaging the equipment.

Figure 8:
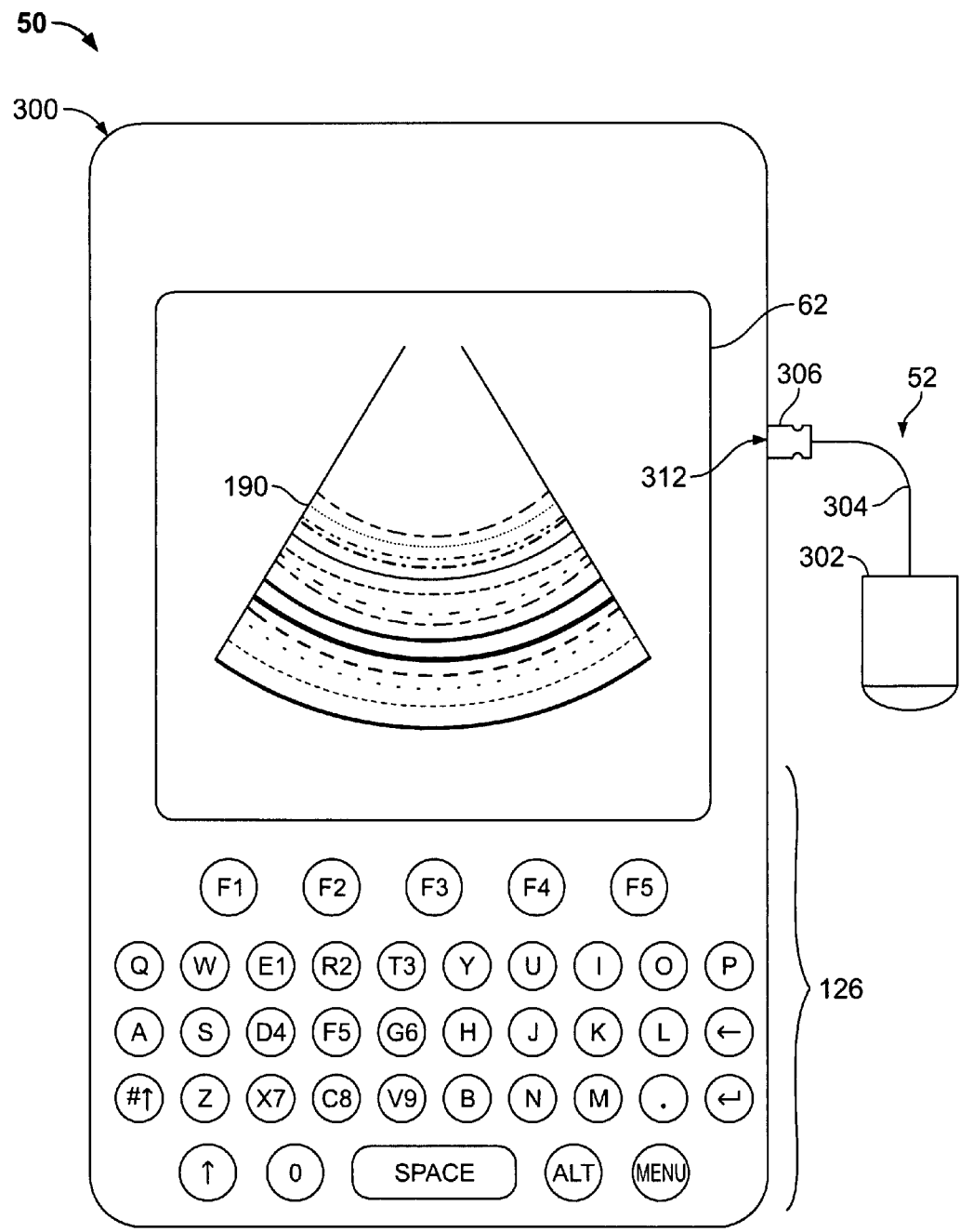
FIG. 8 is a perspective view of a hand carried or pocket-sized medical imaging device constructed in accordance with an embodiment of the invention.

Embodiments of the present invention may be provided in connection with a hand carried imaging system 50 shown in FIG. 8, wherein the display panel 62 and keyboard 125 are both included in unit 300. The hand carried imaging system 50 may be, for example, a handheld or hand carried ultrasound imaging device, such as a miniaturized diagnostic imaging device. As used herein, "miniaturized" means that the diagnostic imaging device is a handheld or hand carried device or is configured to be carried in a person's hand, pocket, briefcase-sized case, or backpack. For example, the hand carried imaging system 50 may be a hand carried device having a size of a typical laptop computer, but without a clam shell foldable configuration. The hand carried imaging system 50 may weigh about ten pounds.

Embodiments of the present invention may also be provided in connection with a pocket-sized imaging system 50, wherein the display 62 and keyboard 126 form a single hand held unit 300. By way of example, the pocket-sized imaging system 50 may be a pocket-sized or hand-sized diagnostic imaging device approximately 2 inches wide, approximately 4 inches in length, and approximately 0.5 inches in depth and weigh less than 3 ounces. The display 62 may be, for example, a 320×320 pixel color LCD display (on which a medical image 190 may be displayed). A typewriter-like keyboard 126 of proximity or capacitive buttons may be included, with labels on the painted side of facade 200. It should be noted that the various embodiments may be implemented in connection with miniaturized imaging systems having different dimensions, weights, and power consumption.

Thus, it will be appreciated that some embodiments of the present invention provide a single piece construction of the user interface and monitor, with no additional framing or peripheral buttons for controlling the scanner. The monitor and hard keys are behind and protected by this single piece. This allows increased cleanability, simplified user interface, increased durability, and over all compact size of the equipment. In embodiments of the present invention that utilize a chemical resistant screen, a clear, built-in protected screen is provided that is chemically resistant to common medical grade antibacterial and antiviral disinfecting agents and does not degrade the ultrasound image. This chemically resistant screen allows protection of the system from fluid splatter and chemical cleaning agents, as well as increase the disinfection of the system as it is quickly and easily wiped clean after every use. Without the need for layered films or cover sheets, the image quality of the screen is kept optimal and films and covers do not need to be purchased and installed.

Furthermore, many embodiments of the present invention have no moving parts to the user interface, no buttons to snap off, and no parts to loosen or come apart at the seams.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A diagnostic medical imaging device comprising:
a display screen mounted in an enclosure and configured for displaying medical images;
a user interface mounted in the enclosure adjacent the display screen and including at least one user input that is operable without moving parts; and
the enclosure including a one-piece non-flexible facade covering the display screen and the user input, wherein the facade is transparent over at least a portion of the display screen and configured such that the at least one user input is operable by a user;
wherein the enclosure is generally box or tablet shaped, the display screen is generally rectangular and mounted on a front surface of the enclosure, and the user interface is adjacent to at least one edge of the display screen and in the enclosure separate from the display screen.

2. The diagnostic medical imaging device of claim 1, wherein the at least one user input is configured to be operated using at least one of a human finger and a stylus.

3. The diagnostic imaging device of claim 2, wherein the at least one user input includes at least one of a proximity switch and a capacitive switch.

4. The diagnostic imaging device of claim 1, wherein the user interface extends along at least two edges of the rectangular display screen.

5. The diagnostic imaging device of claim 1, wherein the generally box or tablet shaped enclosure includes four side edges, the one-piece facade extending over the display screen, the user interface and at least a portion of one of the side edges.

6. The diagnostic imaging device of claim 1, wherein the imaging device is a diagnostic ultrasound imaging system.

7. The diagnostic imaging device of claim 6, wherein the ultrasound system is a portable ultrasound system weighing between about 3 ounces and about 10 lbs.

8. The diagnostic imaging device of claim 1, wherein the at least one user input includes one or more of a soft key, a view position button, a mode button, and a control or operation key.

9. The diagnostic imaging device of claim 8, wherein the at least one user input includes at least one soft key that is assigned different functions on the display screen depending upon at least one of a selected examination mode and a stage of examination.

10. The diagnostic imaging device of claim 9, wherein the different functions include one or more of freeze, store, gain, depth, print, color, patient, measure, comment, Doppler, play, pause, archive, brightness, steer and auto-optimize.

11. The diagnostic imaging device of claim 8, wherein the at least one user input includes at least one mode key configured to control at least one of the display of medical images on the display screen and a change of modes.

12. The diagnostic imaging device of claim 11, wherein the at least one mode key is configured to control at least one of zoom and rotate of a displayed medical image.

13. The diagnostic imaging device of claim 11, wherein the at least one mode key is configured to switch between an examination mode and a viewing mode.

14. The diagnostic imaging device of claim 1, wherein the display screen is a touch screen.

15. The diagnostic imaging device of claim 14, further including a stylus for interacting with at least one of the touch screen and the user input.

16. The diagnostic imaging device of claim 1, wherein the transparent facade has no joints or openings on at least the portion covering the display screen and the user interface to provide increased cleanability and durability for the enclosure.

17. The diagnostic imaging of claim 1, wherein the one-piece facade is thinner over at least one of the display screen and the user interface and thicker over other covered areas.

18. The diagnostic imaging device of claim 1, wherein the transparent facade is a clear polycarbonate plastic.

19. The diagnostic imaging device of claim 1, wherein the one-piece facade comprises one of LEXAN® and CYCOLOY®.

20. A diagnostic medical imaging device comprising:
a display screen mounted in an enclosure and configured for displaying medical images, wherein the display screen is a touch screen;
a user interface mounted in the enclosure adjacent the display screen and including at least one user input that is operable without moving parts;
the enclosure including a one-piece non-flexible facade covering the display screen and the user input, wherein the facade is transparent over at least a portion of the display screen and configured such that the at least one user input is operable by a user; and
a stylus for interacting with at least one of the touch screen and the user input;
wherein the stylus uses an electromagnetic radio frequency signal to interact with at least one of the touch screen and the user input through the transparent facade without any movement of the touch screen or the user input.

21. An ultrasound imaging device comprising:
a display screen mounted in an enclosure and configured for displaying ultrasound images, the enclosure configured to be coupled to an ultrasound probe;
a user interface mounted in the enclosure adjacent the display screen and including at least one user input that is operable without moving parts; and
the enclosure including a one-piece non-flexible facade covering the display screen and the user input, wherein the facade is transparent over at least a portion of the display screen and configured such that the at least one user input is operable by a user;
wherein the enclosure is generally box or tablet shaped, the display screen is generally rectangular and mounted on a front surface of the enclosure, and the user interface is adjacent to at least one edge of the display screen and in the enclosure separate from the display screen.

22. The ultrasound imaging device of claim 21, wherein the at least one user input is configured to be operated using at least one of a human finger and a stylus.

23. The ultrasound imaging device of claim 22, wherein the at least one user input includes at least one of a proximity switch and a capacitive switch.

24. The ultrasound imaging device of claim 21, wherein the user interface extends along at least two edges of the rectangular display screen.

25. The ultrasound imaging device of claim 21, wherein the generally box or tablet shaped enclosure includes four side edges, the one-piece facade extending over the display screen, the user interface and at least a portion of one of the side edges.

26. The ultrasound imaging device of claim 21, wherein the device is a portable system weighing between about 3 ounces and about 10 lbs.

27. The ultrasound imaging device of claim 21, wherein the at least one user input includes one or more of a soft key, a view position button, a mode button, and a control or operation key.

28. The ultrasound imaging device of claim 27, wherein the at least one user input includes at least one soft key that is assigned different functions on the display screen depending upon at least one of a selected examination mode and a stage of examination.

29. The ultrasound imaging device of claim 27, wherein the at least one user input includes at least one mode key configured to control at least one of the display of medical images on the display screen and a change of modes.

30. The ultrasound imaging device of claim 21, wherein the display screen is a touch screen.

31. The ultrasound imaging device of claim 30, further including a stylus for interacting with at least one of the touch screen and the user input, wherein the stylus uses an electromagnetic radio frequency signal to interact with at least one of the touch screen and the user input through the transparent facade without any movement of the touch screen or the user input.

32. The ultrasound imaging device of claim 21, wherein the transparent facade has no joints or openings on at least the portion covering the display screen and the user interface to provide increased cleanability and durability for the enclosure.

33. The ultrasound imaging device of claim 21, wherein the transparent facade is configured to provide a nearly impervious barrier to fluids, scratch resistance, and chemically resistance to cleaning agents commonly used on a medical device.

* * * * *